United States Patent [19]

Rich et al.

[11] Patent Number: 6,099,821
[45] Date of Patent: Aug. 8, 2000

[54] NUCLEAR SCINTIGRAPHIC ASSESSMENT OF MUCOSAL FUNCTION

[75] Inventors: Tyvin A. Rich, Afton; Alexander V. Kirichenko, Charlottesville, both of Va.

[73] Assignees: University of Virginia; University of Virginia Patent Foundation, both of Charlottesville, Va.

[21] Appl. No.: 09/225,979

[22] Filed: Jan. 5, 1999

[51] Int. Cl.[7] .................. A61K 51/00; A61K 103/10; A61K 123/00
[52] U.S. Cl. .................. 424/1.61; 424/1.61; 424/9.1; 424/1.37; 424/1.81
[58] Field of Search ................ 424/1.61, 1.81, 424/9.1, 1.37, 456, 455

[56] References Cited

U.S. PATENT DOCUMENTS

| | | | |
|---|---|---|---|
| 4,243,652 | 1/1981 | Francis | 424/1 |
| 4,670,245 | 6/1987 | Vasquez et al. | 424/1.1 |
| 4,851,209 | 7/1989 | Vasquez et al. | 424/1.1 |
| 4,882,142 | 11/1989 | Simon et al. . | |
| 5,496,828 | 3/1996 | Cullinan | 514/324 |
| 5,804,389 | 9/1998 | Tada | 435/7.1 |
| 5,827,497 | 10/1998 | Camilleri et al. . | |

FOREIGN PATENT DOCUMENTS

| | | |
|---|---|---|
| 0109072 | 5/1984 | European Pat. Off. . |
| 81150326 | of 0000 | Japan . |
| WO96/39622 | 12/1996 | WIPO . |

OTHER PUBLICATIONS

Bellen, J.C., et al., *J. Nucl. Med.*, vol. 36, 513, (1995).
Cionini, L., et al., *Acta Radiol.*, vol. 10, 342, (1971).
Gunter–Smith, P.J., *Rad. Res.*, vol. 117, (Am. J. Physiol., vol. 250, pp. G540–545, 1986), 419, (1989).
Hall, P.A., et al., *J. Cell Sci.*, vol. 107, 3569, (1994).
Krishnamurthy, G.F., et al., *Nucl. Med.*, vol. 12, 97, (1973).
Kwock, L., et al., *Rad. Res.*, vol. 80, 512, (1979).
Medley, C.M., et al., *Brit. J. Radiol.*, vol. 70 Spec., S133–S144, (1997).
Overgaard, J., et al., *Radiother. Onc.*, vol. 18, 71, (1990).
Park, C.H., et al., *Clin. Nucl. Med.*, vol. 21, 375, (1996).
Peters, L.J., *Cancer*, vol. 77, 2379, (1996).
Porvaznik, M., *Rad. Res.*, vol. 78, 233, (1979).
Potten, C.S., *Int. J. Radiat. Oncol. Biol. Phys.*, vol. 58, 925, (1990).
Potten, C.S., et al., *Int. J. Rad. Biol.*, vol. 65, 71, (1994).
Potten, C.S., et al., *Stem Cells*, vol. 15, 82, (1997).
Ruifrok, A.C., et al., *Rad. Res.*, vol. 147, 1, (1997).
Ruifrok, A.C., et al., *Rad. Res.*, vol. 149, 360, (1998).
Thompson, A.R., et al., *J. Lab. Clin. Med.*, vol. 102, 813, (1983).
Thomson, A.R., et al., *Rad. Res.*, vol. 107, 344, (1986).
Tsan, M.F., et al., *J. Nucl. Med.*, vol. 20, 173, (1979).
Withers, H.R., et al., *Int. J. Rad. Biol.*, vol. 17, 261, (1970).
Yeoh, E.K., et al., *Brit. J. Radiol.*, vol. 57, 1131, (1984).
Kegeles et al. American Journal of Physiology 1992;263(5): F963–F973, 1992.
Dorland's Medical Dictionary 27th edition, p. 1494, 1992.

*Primary Examiner*—Jose' G. Dees
*Assistant Examiner*—Shahram Sharareh
*Attorney, Agent, or Firm*—Schwegman, Lundberg, Woessner & Kluth P.A.

[57] ABSTRACT

A method is provided for assessing the functional integrity of a mucosal membrane, comprising: (a) locally administering a dosage of a radionuclide to the surface of a mucosal membrane of a mammal; and (b) employing dynamic scintigraphy to measure the absorption of the radionuclide into the bloodstream of the mammal.

17 Claims, 13 Drawing Sheets

*-mice were irradiated at 10:PM
**- p<0.02

NUCLEAR SCINTIGRAPHIC ASSESSMENT OF MUCOSAL FUNCTION

BACKGROUND OF THE INVENTION

As reviewed by L. J. Peters, in *Cancer*, 77, 2379 (1996), the concept of "treatment to tolerance" is deeply rooted in the practice of oncology. Because relatively few cancers can reliably be cured with chemotherapy and/or radiation therapy, the principle has evolved that treatment should be aimed at the maximum tolerated dose (MTD). Routinely, new treatment strategies undergo Phase I trials in which the MTD is established by dose escalation to the point at which an "acceptable" level of toxicity is encountered. Implicit in this approach is the assumption that the patients enrolled in the Phase I study are representative of the population with the disease, and that the probability of treatment toxicity is dose-related in a predictable way. Neither of these assumptions is true if the patient population is heterogeneous with regard to susceptibility to toxicity; and the MTD determined from a limited Phase I study cannot be assumed to have general applicability.

With chemotherapy, unlike radiotherapy, toxicity is mostly acute or cumulative, and since treatment is usually administered cyclically, the lack of a well-defined MTD can be partially circumvented by titrating the dose given to each patient to conform to his or her individual tolerance. Conversely, definitive radiation is given as a single course, and is dose-limited in the main by toxicities that develop after therapy is completed. Thus, any concept of MTD has to be based on probabilistic estimates of the risk of injury for the population as a whole.

Acute mucosal damage, such as damage to the intestine can be a major dose-limiting event in radiation therapy and chemotherapy, and has been extensively studied in the laboratory regarding the cellular mechanism of injury. Aspects of rapid cell turnover, distinct compartmentalization of damage, and known differentiation pathways of crypt cells in the murine and human intestine have been well studied. See, for example, C. S. Potten, *Int. J. Radiat. Oncol. Biol. Phys.*, 58, 925 (1990). Treatment effect after cytotoxic chemotherapy or irradiation has been evaluated by apoptosis induction, and the classically by crypt colony assay. H. R. Withers et al., *Int. J. Rad. Biol.*, 17, 261 (1970); A. C. Ruifok et al., *Rad. Res.*, 149, 360 (1998). The former is a very sensitive method that may saturate at 1 Gy, and the latter has a threshold at doses of 8 to 9 Gy. See, C. S. Potten et al., *Int. J. Rad. Biol.*, 65, 71 (1994); Withers et al., cited supra.

Functional disorders of the intestine including those created by ionizing irradiation can be measured by abnormalities in absorption of various nutrients including glucose, vitamin B12, D-xylose and bile acids. For example, see A. B. R. Thompson et al., *Rad. Res.*, 107, 344 (1986). Most of these studies have been performed on rodents using either in vivo or in vitro perfusion techniques, and have limited clinical application (J. Overgaard et al., *Radiother. Onc.*, 18, 71 (1990)). One of the earliest functional changes seen with irradiation of the gut is a disturbance of ATP-dependent transport of nutrients through the intestinal epithelial cells which include changes in the maximal velocity, the Michaelis constant and incremental changes in free energy (A. B. R. Thompson et al., *J. Lab. Clin. Med.*, 102, 813 (1983)). The reduction in the active transport of glucose across the jejunal mucosa following irradiation has been tightly correlated with the epithelial surface area available for the absorption by P. J. Gunter-Smith, *Rad. Res.*, 117, 419 (1989) and J. Overgaard et al., cited supra, and the authors suggested this could be used clinically to detect radiation damage to the intestine in relationship with epithelial cell loss.

Thus, a continuing need exists for new methods to assess treatment effects that are sensitive to cytotoxic treatment in clinically relevant dose ranges, that are noninvasive, and that could allow for repeated assessment in the same subject to understand the time course of cytotoxic insult.

SUMMARY OF THE INVENTION

The present invention provides a nuclear medicine technique using mucosal absorption of a radionuclide to study radiation-induced mucosal damage, such as damage to the intestinal mucosa due to a chemotherapy or radiation therapy. The absorption correlates to morphological changes in the epithelium. More specifically, the present invention provides a diagnostic method for assessing the functional integrity of a mucosal membrane, comprising: (a) locally administering a dosage of a radionuclide to the surface of a mucosal membrane of a mammal; and (b) employing dynamic scintigraphy to measure the absorption of the radionuclide into the bloodstream of the mammal; wherein said absorption provides a measure of the functional integrity of the mucosal membrane. Typically, after step (b), the mammal is subjected to radiation therapy and/or chemotherapy effecting said mucosal membrane and steps (a) and (b) are repeated to provide an indication of the progressive loss of said functional integrity. Thus, the absorption of the radionuclide decreases following therapy, and the decrease is correlated to the extent of damage to the mucosal membrane. Repetition of the assay after successive rounds of therapy permits the oncologist to adjust the therapy to achieve the maximum tolerated dose, while retaining sufficient function in the adversely effected organs or vessels of the subject. Thus, the absorption of the radionuclide or other tracer provides a measure of the tolerance of said mammal to the treatment regimen. Mucosal membranes typically subject to damage due to cancer therapies include the membranes of the gastrointestinal tract, respiratory tract, the mouth, nasal tract, throat and esophagus, and the urogenital tract.

The method described experimentally here is based on the measurement of the velocity of absorption and this can be accomplished by an automated computerized system. The dynamic enteroscintigraphy with technetium pertechnetate is a sensitive functional assay for the rapid evaluation of the chemotherapy and radiation-induced intestinal damage in clinically useful dosage ranges. The decrease in the intestinal absorption function has a cellular basis and correlates with the number of cell losses per villus in a dose-dependent fashion.

As used herein, the term "absorption" refers to the transport of a substance from the interior or exterior mucosal surface across the mucosal membrane into the blood.

BRIEF DESCRIPTION OF THE INVENTION

DETAILED DESCRIPTION OF THE INVENTION

Preferably, scintigraphy is employed to measure the relative amount of the radionuclide or radiotracer, at a site remote from the site of administration. This method can be applied to evaluate the absorption function in preselected sites of the gastrointestinal tract from the mouth cavity to the rectum. This method can also be used to detect the cross-mucosal transport in nasal cavity, urogenital tract, all segments of the respiratory tract as well as absorption of the labeled compounds through exterior surfaces (skin, conjunctiva, genitalia) and nonmucosal surfaces (peritoneal, pleural, CNS).

To register the tracer presence in the body, all radiological methods of visualization or dynamic radiometry can be used. Detectors can be placed outside the body or inside (oral cavity, rectum or IV on the tip of catheter).

For example, the radionuclide may be administered parenterally to the intestinal tract and the radionuclide may be measured in the bloodstream at the heart. The present method can be used to evaluate absorption in animal models, as well as to evaluate the course of treatment of human patients.

Any radionuclide or mixture of radionuclides can be employed that is absorbed by the mucosal membrane of the target organ, tissue or vessel and which is detectable by scintigraphy. Such radionuclides (or radioisotopes) include technetium-99m ($^{99m}Tc$), selenium-75 ($^{75}Se$) and the radioisotopes of iodine, e.g., iodine-131. As used herein, the term radionuclide or radioisotope includes ionic forms of these metals, such as their nontoxic salts, as well as any organic chelating agent that may be associated therewith, such as DTPA, TTHMP, NTMP, EDTMP, DTPMP, EDTA, DOTMP, cyanocobalamin or carriers, such as HSA and tyrosine. See L. Cionini et al., *Acta Radiol.*, 10, 342 (1971); E. K. Yeoh et al., *Brit. J. Radiol.*, 57, 1131 (1984); U.S. Pat. No. 4,882,142; C. M. Medley et al., *Brit. J. Radiol.*, 70 *Spec.*, S133–S144 (1997). Other radionuclides and salts thereof useful in the practice of the invention are disclosed in U.S. Pat. No. 5,827,497. Dual radioactive isotopes or a combination of radioisotopes with non-radioactive tracers can be used. Photosensitizers or fluorescent dyes and nutrients such as amino acids, carbohydrates, electrolytes, vitamins, hormones, and the like can be used as tracers in modifications of this method.

Local or site-specific administration of the radionuclide to the target mucosal membrane may be accomplished by parenteral methods, such as injection or infusion. Tracers can be delivered also through catheters under direct visualization by endoscopy or by intraluminal injection at surgery. The radionuclide can also be delivered from a transmucosal patch or hydrogel insert.

The radionuclide can also be delivered orally, i.e., by an enteric-coated dosage form such as a tablet, capsule or pill. Radionuclide can be delivered by mouth in capsules designed for the rapid remote, and controlled release of the radionuclide in the target site of the GI tract. The timed release of the tracer from a capsule may be controlled through chemical, electromagnetic, radiowave-sensitive, light-sensitive, ultrasound or ionizing-radiation-sensing mechanisms. A patient can also swallow a controlled release dosage form, such as a capsule, that can be manipulated, i.e., via a guide wire, or otherwise programmed or directed, to release a composition comprising the radionuclide or non-radioactive tracers at the target site.

The radionuclide is preferably dissolved or dispersed in a suitable liquid vehicle, i.e., many metal salts may simply be dissolved in water or in physiological saline. The appropriate amount will depend on a number of factors, as would be appreciated by the clinician, including area to be evaluated, size, age and condition of the patient, radionuclide selected, area of membrane to be evaluated and the like.

The present method can be used to test the absorption of all nutrients (amino acids, carbohydrates, lipids, vitamins, minerals and trace elements), as well as pharmacological compounds and xenobiotics labeled with radioactive isotopes (including β- and γ-emitters).

In the example hereinbelow, jejunal absorption of $^{99m}$Technetium-pertechnetate, an actively transported γ-emitter, was assessed in mice exposed to total body irradiation (4, 6, 8 and 12.5 Gy) and correlated with morphological changes in the intestinal epithelium. $^{99m}$Technetium-pertechnetate absorption from the intestinal lumen into the circulation was studied with a dynamic gammascintigraphy assay combined with a multichannel analyzer to record the radiometry data automatically in a time-dependent regimen. The resulting radioactivity/time curves obtained from irradiated animals were compared to the control group that received no irradiation, and statistically evaluated with mathematics modeling. Intestinal absorption decreased in a dose-dependent fashion when assessed after irradiation. The jejunal absorption of the tracer infused into the jejunum lumen was lowest after 12.5 Gy whole body irradiation and dropped to nearly 25% of the control level. By this time, the mean rate of the tracer absorption was significantly delayed even by sublethal 4 Gy total body irradiation in comparison with control values (1.51±0.15 and 1.35±0.25 respectively). Decrease in the $^{99m}$Technetium-pertechnetate absorption at 3.5 days after irradiation correlated with the numbers of cells per villus and the irradiation dose in the range of 4 to 12.5 Gy. By this time, the total number of apoptotic cells in the crypt compartment had gradually increased in the dose-dependent fashion between 4 and 12.5 Gy from a normal background of less than 0.5–3.6% after 8.0 Gy irradiation. In contrast, the jejunal microcolony assay showed no difference in the number of surviving crypts between control animals and mice irradiated at 4, 6 and 8 Gy.

EXAMPLE 1

Dynamic Scintigraphy Assay of Jejunal Absorption After Irradiation

A. Methods and Procedures

Inbred 3 to 4 month old C3Hf/Kam female mice were obtained from a mouse barrier, pathogen-free facility at Experimental Radiotherapy Department, M. D. Anderson Cancer Center (Houston, Tex.). Mice were housed four per cage under 12 hour light/dark cycles (lights on at 6 a.m.) at about 23° C. and supplied standard food and water ad libitum.

The effect of irradiation on pertechnetate ($^{99m}TcO^-_4$) absorption in the mouse jejunum was studied in situ following single acute total body irradiation (TBI) with 4 Gy, 6 Gy, 8 Gy, and 12.5 Gy. During irradiation, three unanesthetized mice were placed in a 20×20×3.5 cm air-ventilated plastic jig and exposed to a single-source $^{60}Co$ irradiator (Theratron 780-C) at a dose rate of 120 Gy/minute, with open irradiation field and 71 cm SSD. This setting assured homogeneous dose distribution within ±3% error.

Four to five mice per irradiation dose of 4 Gy, 6 Gy, 8 Gy and 12.5 Gy per day after irradiation (6 Gy irradiated group) were studied for the intestinal absorption function. The mice were fasted overnight (waster ad libitum) and then anesthetized with 100 μL of 1.5 mg/g ketamine solution injected intraperitoneally. The procedure began with a short midline incision of the abdomen after onset of deep anesthesia, and a 3 cm segment of the upper jejunum was identified, ligated with cotton sutures and catheterized with 0.2 mm flexible plastic catheter.

Next, the abdomen incision was closed with cotton sutures and the mouse was positioned under the collimated detector so the 1.5 cm window of the collimator was viewed at the heart projection with 0.2 cm skin-to-collimator distance. A 100 μL physiologic solution containing 100 μCi of Na($^{99m}TcO_4$) was rapidly injected through the catheter into the proximal end of the isolated jejunal segment with complete filling of the entire segment.

The absorption rate of $^{99m}TcO^-_4$ from the site of injection into the circulation was recorded automatically by measuring the relative radioactivity build-up rate above the heart projection with the frequency of two measurements per second. The entire dynamic enteroscintigraphy procedure took about 15 minutes in control mice. The systemic absorption of the pertechnetate ($^{99m}TcO^-_4$) was performed on a standard scintillation radiometer combined with a multichannel analyzer (Ludlum Measurements, Sweetwater, Tex.) to record the radiometry data in time-dependent fashion. The software ULTIMA-4 was used to receive the graphic imaging of the dynamic radiometry data.

Measured activity/time curves detected above the heart are mathematically modeled as exponential saturation of the form $y(t)=y0+dy\{1-\exp[-k(t-t0)]\}$; where $y(t)$ is the observed time-dependent radioactive counts above the heart; $y0$ is the observed activity at time of tracer introduction, $t0$; $dy$ is the magnitude of the change in radioactive counts after tracer introduction; and $k$ is the rate constant characteristic of the active transport of tracer through the intestinal wall into the systemic blood circulation. Analyses of tracer absorption kinetics by this expression allow precise statistical assessment of radiation-induced functional impairment of the jejunal active transport process.

At 3.5 days after irradiation with 4, 6, 8 and 12.5 Gy and immediately upon completion of the absorption study, groups of 4–5 mice per radiation dose were killed by cervical dislocation and a 2-cm length of jejunum was removed for histological preparation. Intestinal segments were fixed in 10% neutral buffered formalin. Four transverse sections of intestine were prepared embedded into paraffin, cut at a thickness of 4 μm and stained with hematoxylin and eosin (H&E). Slides with tissue sections were examined with light microscopy under 400-power magnification. A total of 500 crypt cells per mouse form 12–16 complete crypts were scored as mitotic or apoptotic. The jejunum microcolony assay of H. R. Withers et al., *J. Rad. Biol.*, 17, 261 (1970) was used to quantify jejunal crypt survival. Tissue sections were scored microscopically using 100-power magnification. Surviving crypts contained at least 10 tightly packed columnar epithelial cells located in the base of the crypt (discrete cell microcolonies). The number of surviving crypts/circumference of jejunum was plotted as a function of radiation dose in Gy.

B. Results

1. Absorption assay. The intestinal absorption was studied in control animals in order to evaluate the $^{99m}TcO^-_4$ transport mechanism. Rapid absorption of the tracer occurs from the intestine lumen into the bloodstream. Similar rapid intestinal absorption was obtained with $^{131}$Iodine. Simultaneous co-administration of 1 mg/kg $KClO_4$ and Na$^{99m}TcO_4$ into the intestinal lumen of the control mice shifted the saturation point on the radioactivity/time curve to the right without changes in the amount of the absorbed tracer.

Figure 1:
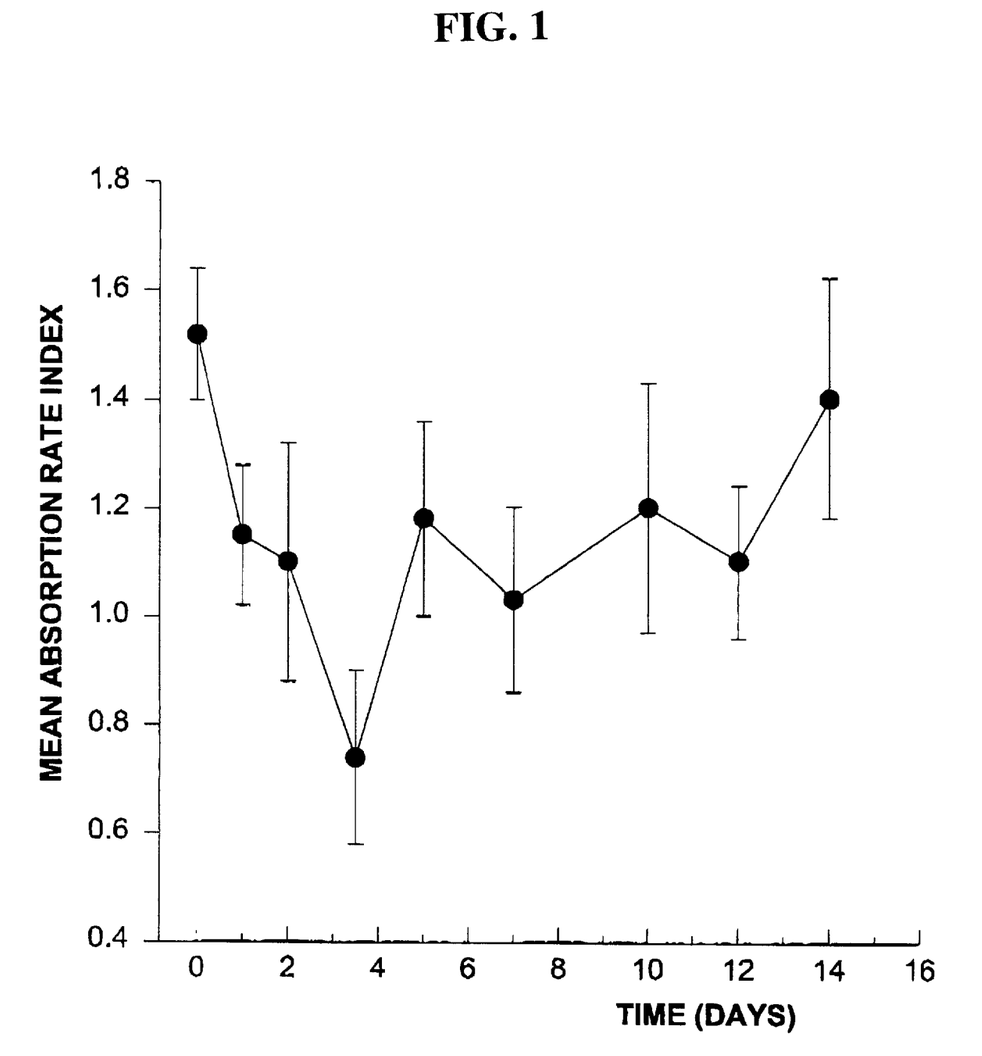
FIG. 1 is a graph depicting the dynamic of $^{99m}TcO_4^-$ absorption rate in the jejunum of C3Hf/Kam mice after 6.0 Gy of total body irradiation (TBI).

The time course of the absorption function after 6 Gy whole body irradiation is shown in FIG. 1. There was a significant decrease in the absorption function at 24 hours after irradiation, reaching its minimal value on the 3.5 day after irradiation. The absorption rate gradually returned to a normal level in about 14 days.

Figure 2:
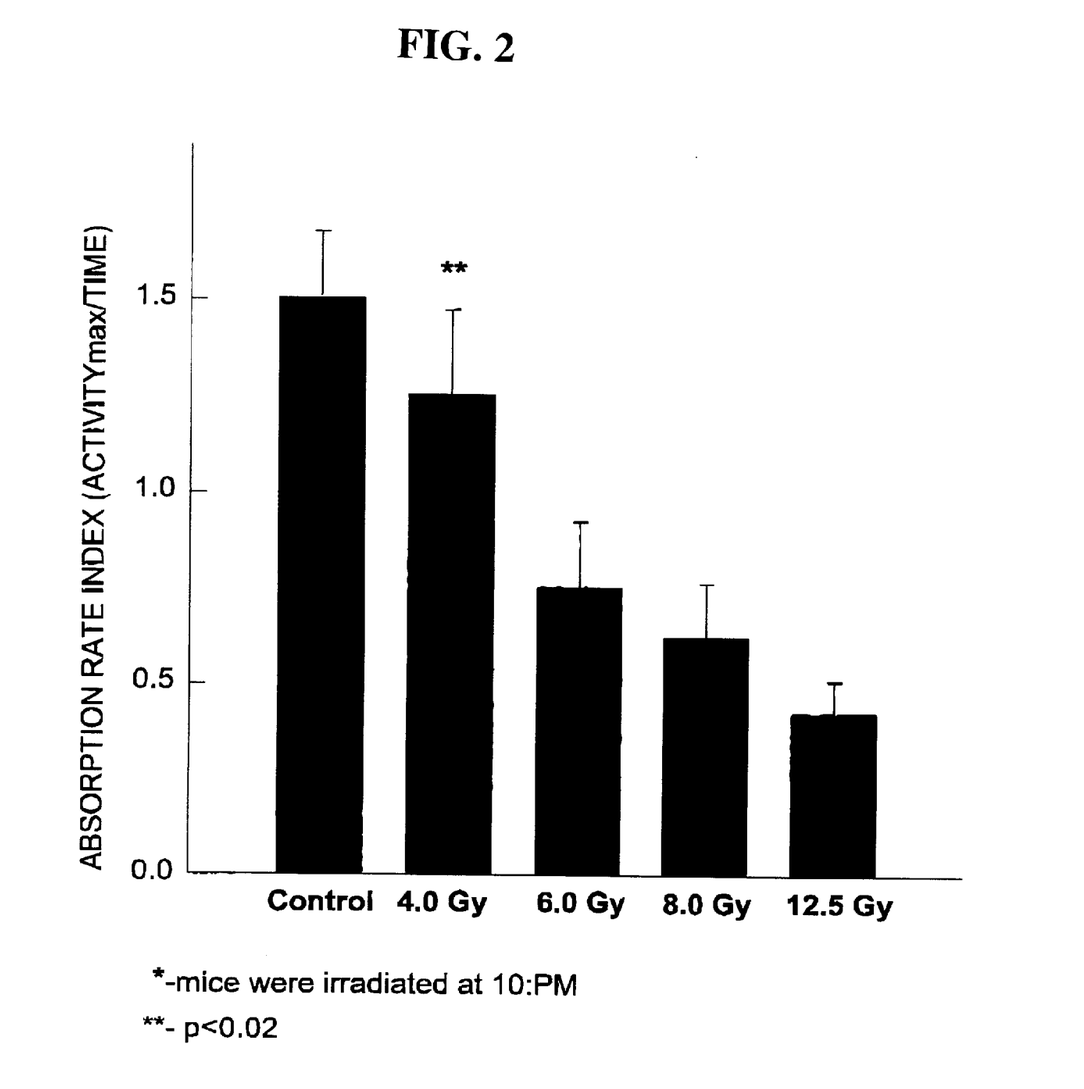
FIG. 2 is a graph depicting the absorption rate index of $^{99m}Tc$ in the jejunum of C3H mice 3.5 days after TBI.

A substantial dose-dependent decrease in the absorption function was observed 3.5 days following irradiation. The absorption of the tracer infused into the jejunum lumen had the lowest rate after the 12.5 Gy whole body irradiation reaching values near 25% of the control level (FIG. 2). By this time, the mean rate of the $^{99m}TcO^-_4$ intestinal absorption was significantly delayed even by sublethal 4 Gy total body irradiation in comparison with control values (1.51±0.15 and 1.35±0.25 respectively).

To exclude a role of simple diffusion ("leakage") of the tracer through the irradiated GI mucosa studies of the intestinal permeability with $^{67}$Ga-citrate complex introduced into the jejunal lumen at 84 hours after exposure to 12.5 Gy were performed. The data indicate that jejunal mucosa stays impermeable for the $^{67}$Ga-citrate introduced intraluminally at any time of the first 7 days after mice total body irradiation.

Figure 3:
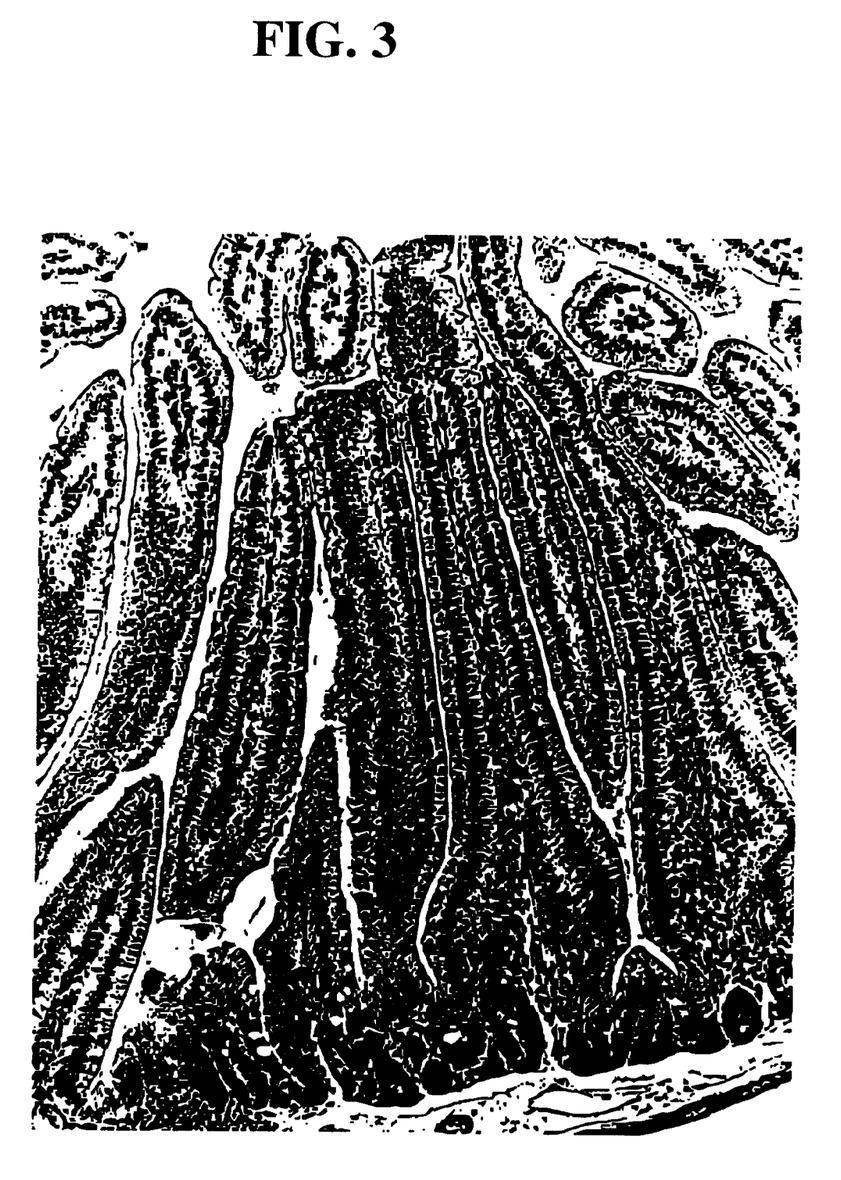
FIG. 3 depicts typical appearance of normal mouse jejunal mucosa.
Figure 4:
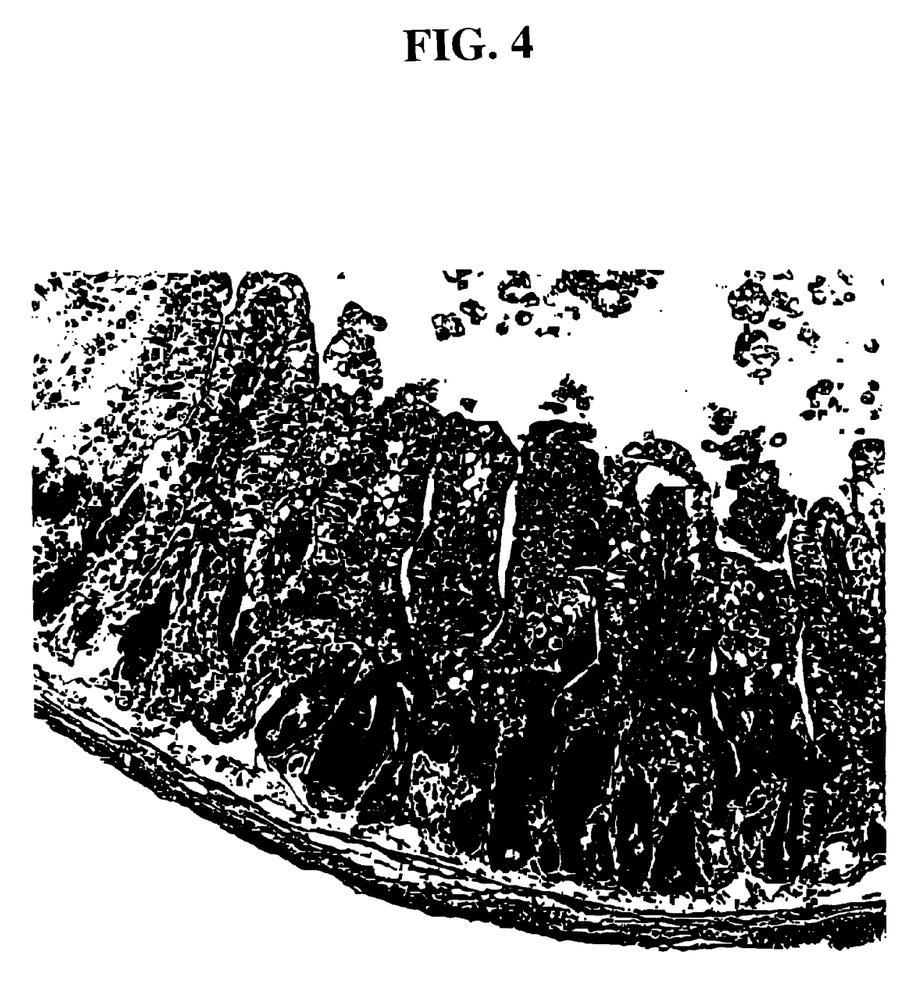
FIG. 4 depicts appearance of damaged mouse jejunal mucosa after 12.5 Gy of TBI.

2. Morphology. The morphology of the jejunal segment used in the absorption studies was evaluated in attempt to define underlying factors in the absorption function changes following radiation exposure. FIG. 3 shows typical appearance of the normal jejunal mucosa. In mice irradiated in the 4 to 12.5 Gy dose range, the progress of the intestinal injury was similar regardless of the exposure dose, but the severity of the damage such as villus cell loss, number of apoptotic cells in the crypt as well as number of surviving crypts in the intestine was dose dependent and reached its maximal level after 12.5 Gy (FIG. 4).

Figure 5:
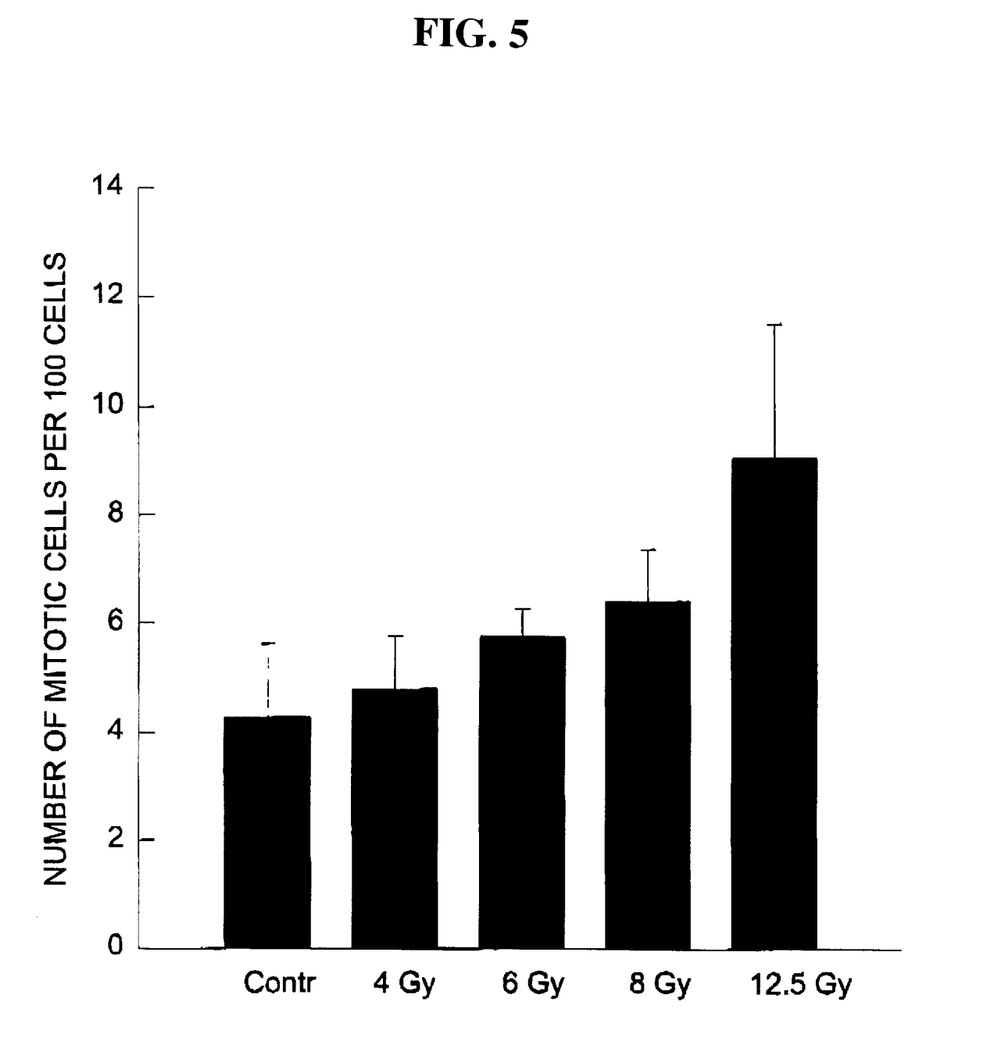
FIG. 5 is a graph depicting the number of mitotic jejunal mucosa cells at 3.5 days after various doses of TBI.
Figure 6:
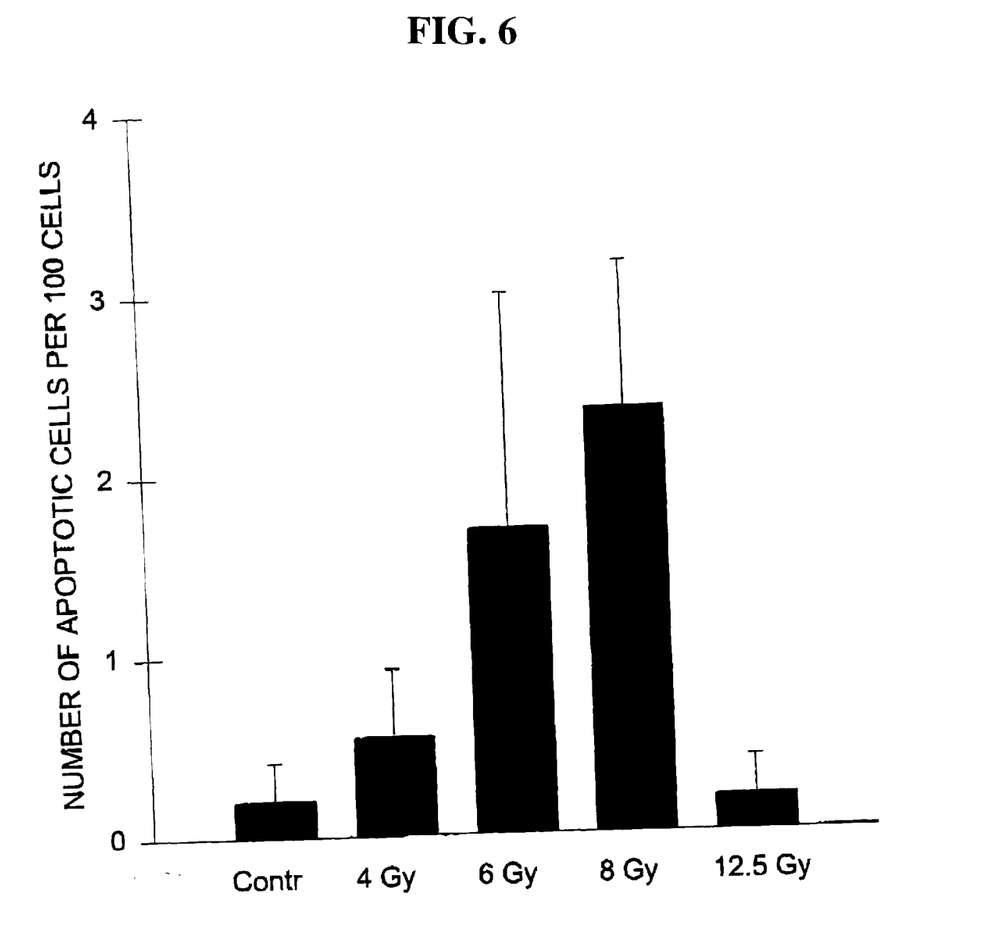
FIG. 6 is a graph depicting the number of apoptotic jejunal mucosa cells at 3.5 days after various doses of TBI.
Figure 7:
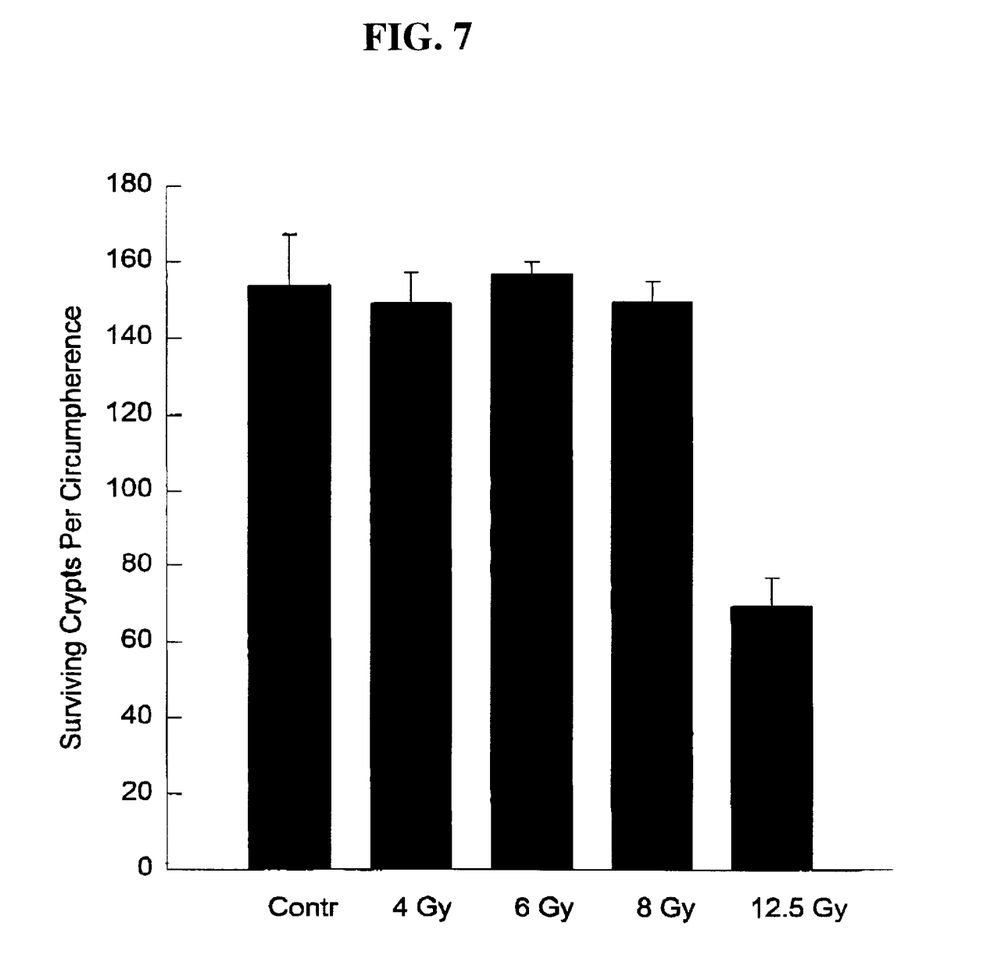
FIG. 7 is a graph depicting the number of surviving crypts/transverse histological section of mouse jejunum 3.5 days after various doses of TBI.

Crypt damage appeared early after total body irradiation with 12.5 Gy although the villi remained long and the covering columnar epithelium showed little changes until 84 hours postexposure. By 84 hours after irradiation, there was extensive regeneration in the crypt compartment with numerous mitotic figures in the entire crypt area. At this time, the number of mitotic crypt cells was increased in parallel with increasing irradiation dose (FIG. 5). Apoptotic bodies appeared as small, condensed membrane-bound cellular fragments with condensed cytoplasm, and usually contained sharply defined masses of condensed chromatin. At 84 hours, the total number of apoptotic cells in the crypt compartment had increased in a dose-dependent fashion from a normal background level of less than 0.5 to 3.6% after 12.5 Gy irradiation (FIG. 6). At this time, the jejunal microcolony assay showed no difference in the number of surviving crypts between mice irradiated at 4, 6 and 8 Gy and control animals however, irradiation with 12.5 Gy resulted in about 50% of the jejunal crypt death (FIG. 7).

Figure 8:
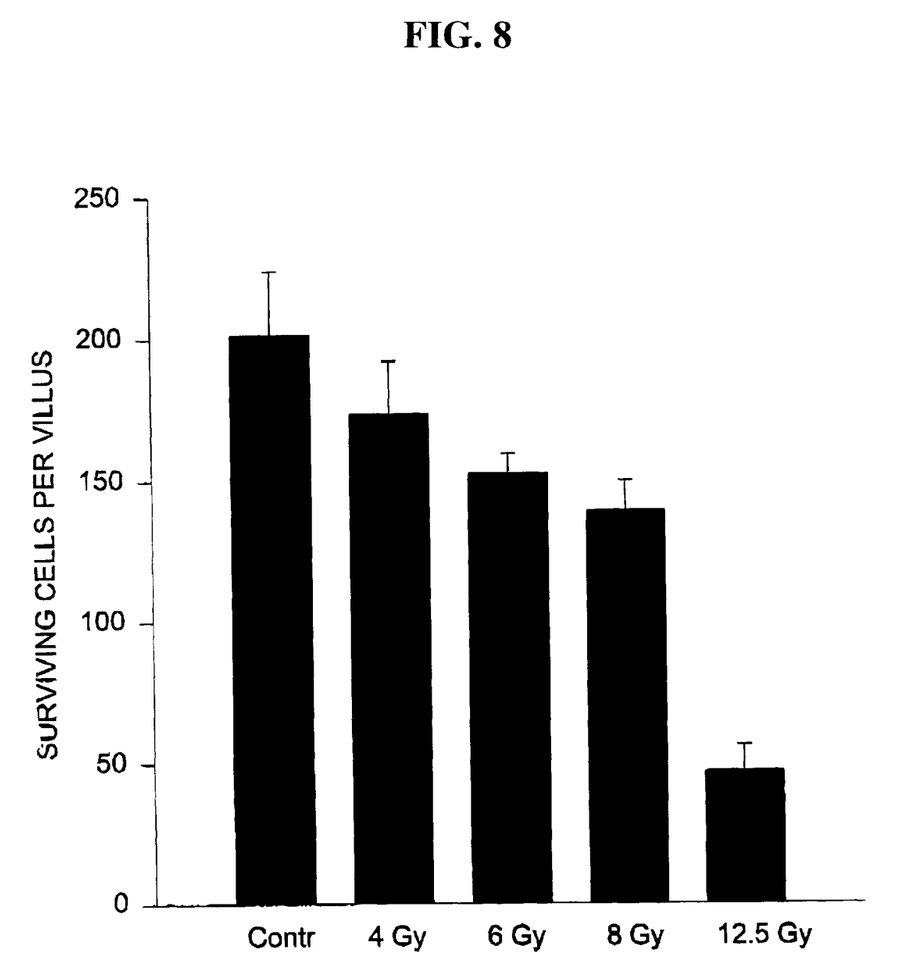
FIG. 8 is a graph depicting the number of cells per villus of mouse jejunum 3.5 days after various doses of TBI.

Eighty-four hours after single total body irradiation over the range of 4 to 12.5 Gy, dose-dependent morphological changes occur in the non-proliferative compartment of the intestinal epithelium. The villi were shortened, the high cylindrical epithelium of the villi was reduced to flat, vacuolated, cuboidal epithelium, and the number of epithelial cells lining villus surface was substantially decreased in a dose-dependent fashion (FIG. 8). Following 12.5 Gy whole body irradiation, near 50% of mice died within the first 8 day interval at a time when the crypts were largely repaired, but the villi were substantially damaged.

C. Discussion

The choice of technetium pertechnetate in this study was based on its active transport system, that is similar or the same as for iodine ion (G. F. Krishnamurthy et al., *Nucl. Med.*, 12, 97 (1973)). In addition, $^{99m}TcO^-_4$ is known as one of the least radiotoxic nuclides used in the nuclear medicine, featuring as pure γ-emitter with optimal energy spectrum for the detection (140 keV), relatively short half-life (6 hours), low metabolic activity and low cost (C. M. Medley et al., *Brit. J. Radiol.*, 70 *Spec.*, S133–144 (1997)). To determine whether $^{99m}TcO^-_4$ is transported similarly to iodine, kinetic parameter studies with $^{131}I$ absorption were initially performed. The same shape of the $^{99m}TcO^-_4$ intestinal absorption curve was obtained for 131I with specific active transport kinetic parameters such as rapid tracer absorption and subsequent saturation. Experiments with potassium perchlorate, which is a known competitive inhibitor of the technetium pertechnetate active transport, provide additional support for evaluation of the nature of the $^{99m}TcO^-_4$ cross-membrane transport. See, C. H. Park et al., *Clin. Nucl. Med.*, 21, 375 (1996).

In order to evaluate if $^{99m}TcO^-_4$ absorption remains an active transport process in irradiated animals rather than passive diffusion or "leakage" phenomenon, studies were performed on irradiated gut permeability with $^{67}Ga$ citrate complex. Morphological observation that high doses of irradiation cause intestinal mucosal denudation and decrease in the integrity of the tight junction between the epithelial cells on the villi by M. Porveznik, *Rad. Res.*, 78, 233 (1979), are in agreement with the present observation. It has been shown earlier that $^{67}Ga$-citrate normally does not cross the intestinal epithelial barrier and thus has been used in the gastric and colonic transit studies (J. C. Bellen et al., *J. Nucl. Med.*, 36, 513 (1995)) On the other hand, inflammation or local hyperthermia induce plasma membrane permeability and consequently augments $^{67}Ga$-citrate accumulation in the sites of lesion by simple physical diffusion of the citrate ion (M. F. Tsan et al., *J. Nucl. Med.*, 20, 173 (1979)).

These data indicate that the jejunal mucosa stays impermeable for the $^{67}Ga$-citrate introduced intraluminally after 12.5 Gy TBI and confirms previous observations that possible radiation-induced disruption of the epithelial integrity with denudation of the intestinal mucosa is of little consequence to postirradiation active cross-mucosal transport (P. J. Gunter-Smith, *Rad. Res.*, 117, 419 (1989); *Am. J. Physiol.*, 250, G540–545 (1986)).

Using the remote dynamic scintigraphy technique, it was determined that single dose of TBI with 4 Gy, 6 Gy, 8 Gy and 12.5 Gy significantly decreases $^{99m}TcO^-_4$ jejunal absorption. The maximal reduction occurred 84 hours after irradiation independently of doses used. The degree of the malabsorption was strongly dose dependent with a steep dose-response relationship observed 84 hours after irradiation (FIG. 2). By this time, morphological evaluation of mouse jejunum showed maximal and dose-dependent cell loss on the villus (FIG. 4) with the normal structure and cellularity in the crypt compartment in the dose range between 4 Gy and 8 Gy (FIG. 3). Most animals exposed to 12.5 Gy to the total body subsequently died within the first 8 days after irradiation when a majority of the crypts had normal structure but the villi showed their greatest damage and cell loss. The absorption function in these mice was reduced to less than 25% of the control level (FIG. 2). These observations suggest that the decrease in the intestinal absorption activity in response to irradiation has a cellular basis.

A significant effect of 6 Gy irradiation on the intestinal $^{99m}TcO^-_4$ absorption activity was observed as early as 24 hours after irradiation (FIG. 1). This early reduction of the absorption function is more likely to be attributed to a loss of functionally active cells on the villi. It has been shown by A. C. C. Ruinfrok et al., *Rad. Res.*, 147, 1 (1997), that the total villus cellularity is reduced from about 185 to about 160 cells per villus on the first day after 5 Gy TBI. Since there is early apoptotic death plus temporary mitotic block in the crypt region, and yet a continued unaffected cell migration, the villus can potentially be cell depleted as early as 24 hours after sublethal irradiation (C. S. Potten et al., *Stem Cells*, 15, 82 (1997)). Early villus cell depletion along with reduction in the intestinal absorption function may be due to radiation-induced apoptosis either in the upper crypt region or in the base of the villus which both are equally active in the absorption function. At this point, the epithelial transport activity may itself be a measure of cell viability, as decreased carried-mediated active transport of nutrients preceded cell death, possibly by apoptotic mechanism (L. Kwock et al., *Rad. Res.*, 80, 512 (1979)). It was also reported by P. A. Hall et al., *J. Cell Sci.*, 107, 3569 (1994) that apoptosis does indeed occur in the non-proliferative villus region regulating epithelial population size in normal physiological conditions, although occurrence of the radiation-induced apoptosis in the villus cells remain to be demonstrated.

By 3.5 days after the exposure with 4 to 8 Gy, all crypts had normal structure but apoptotic cell death in this region was still evident (FIG. 6). Thus, continued apoptotic crypt cell death after 6 Gy TBI may contribute to the villus cell deficit with subsequent reduction in the absorption activity observed for the next 10 to 12 days after irradiation (FIG. 1).

EXAMPLE 2

Dynamic Scintigraphy Assay of Jejunal Absorption after Chemotherapy or Combined Chemoradiotherapy.

C3H female mice, 11–13 weeks of age, were used in this study. To assess the changes in the intestinal absorption function, groups of mice were given: a) a single (4 mg/kg) intramuscular dose of 9-aminocamptothecin (anticancer chemotherapeutic drug targeting DNA topoismerase I, characterized by pronounced GI toxicity); b) a single dose of 4 Gy total body irradiation; c) a single (2 mg/kg) intramuscular dose of 9-aminocamptothecin; and d) a combination of single 2 mg/kg 9-AC and a single dose of 4 Gy total body irradiation.

The dynamic enteroscintigraphy with $^{99m}$Tc-pertechnetate and the morphology studies were performed as described above in Example 1.

Figure 9:
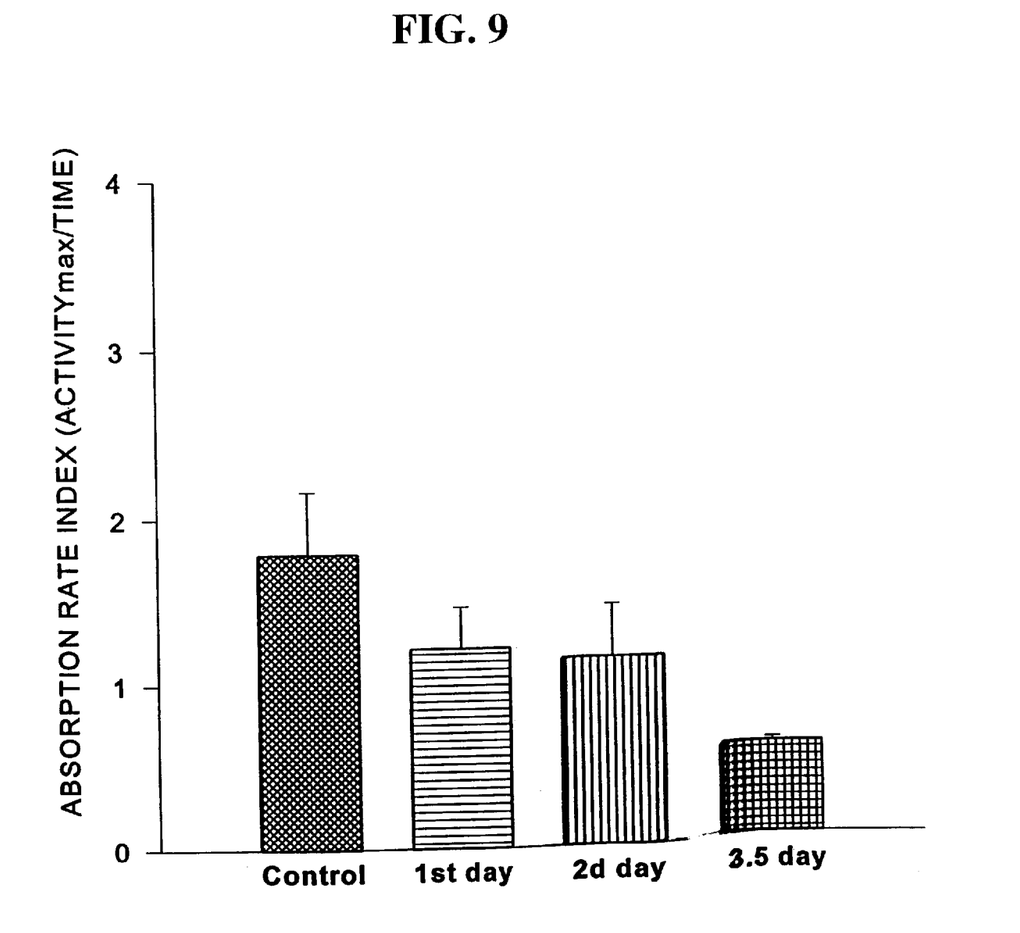
FIG. 9 is a graph of the absorption rate index of $^{99m}TcO^-_4$ in the jejunum of C3H mice after 9-aminocamptothecin injection (1×10 at 4 mg/kg).
Figure 10:
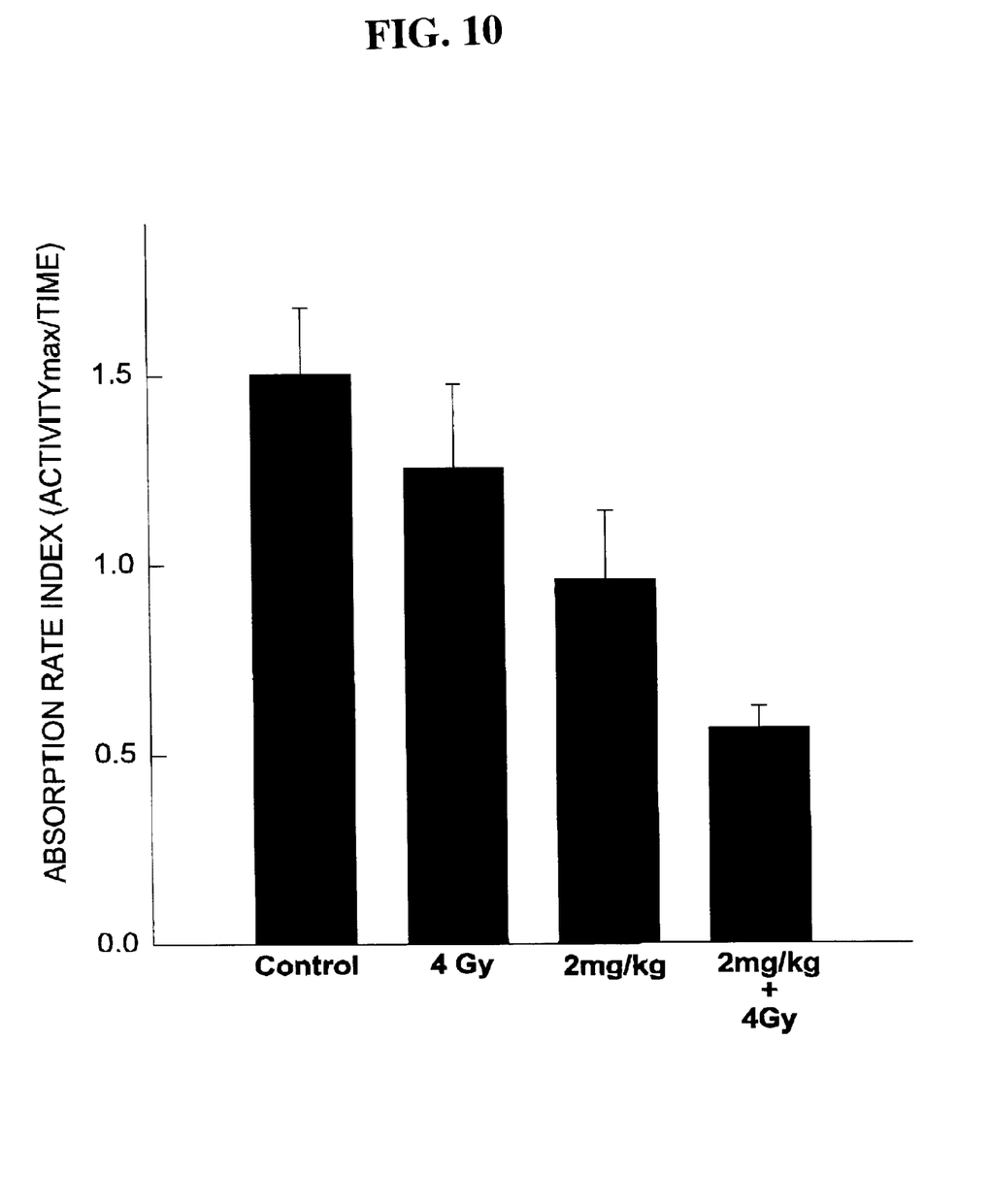
FIG. 10 is a graph of the absorption rate index of $^{99m}TcO^-_4$ in the jejunum of C3H mice on day 3.5 after single 9AC injection combined with 4 Gy TBI.
Figure 11:
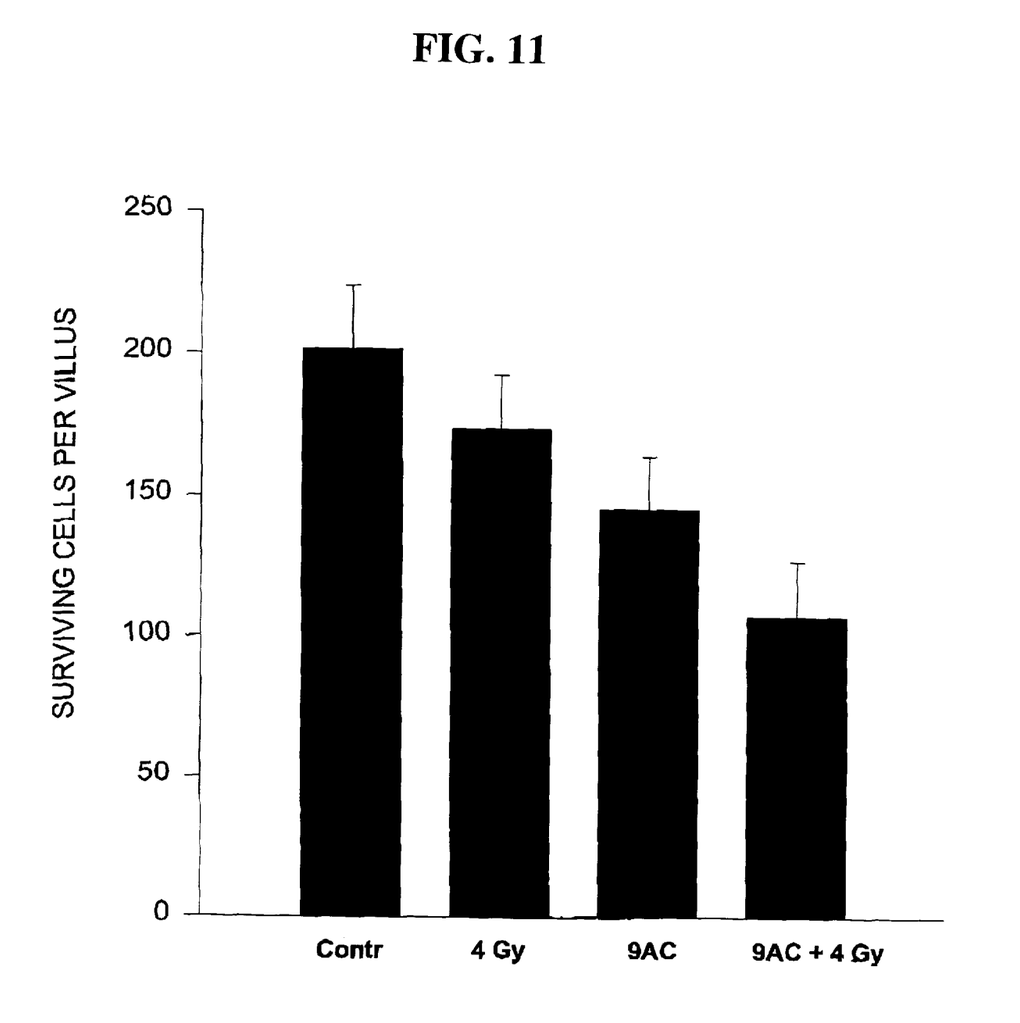
FIG. 11 is a graph depicting the number of cells per villus of mouse jejunum after 9AC injection and/or TBI.
Figure 12:
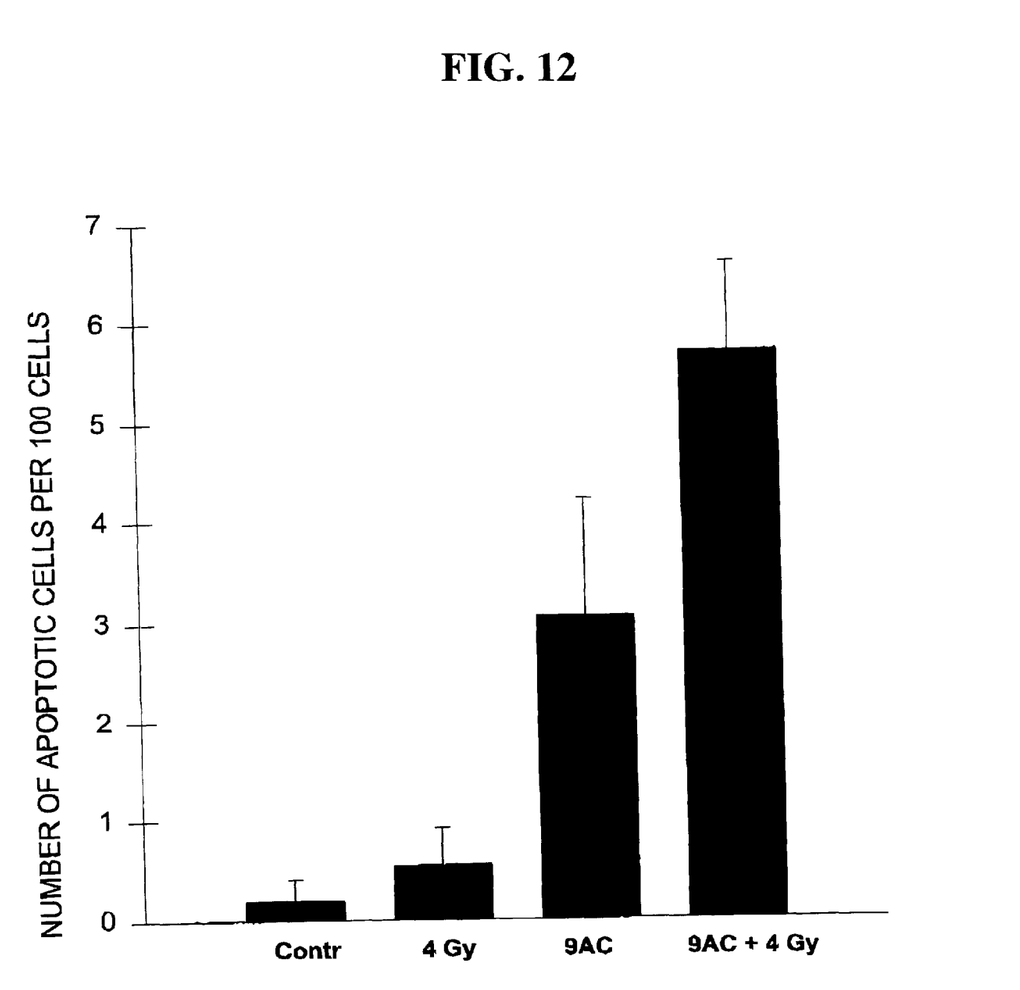
FIG. 12 is a graph depicting the total number of apoptotic cells in mouse jejunum 3.5 days after 4 GY TBI, single 2 mg/kg 9AC injection or both agents.
Figure 13:
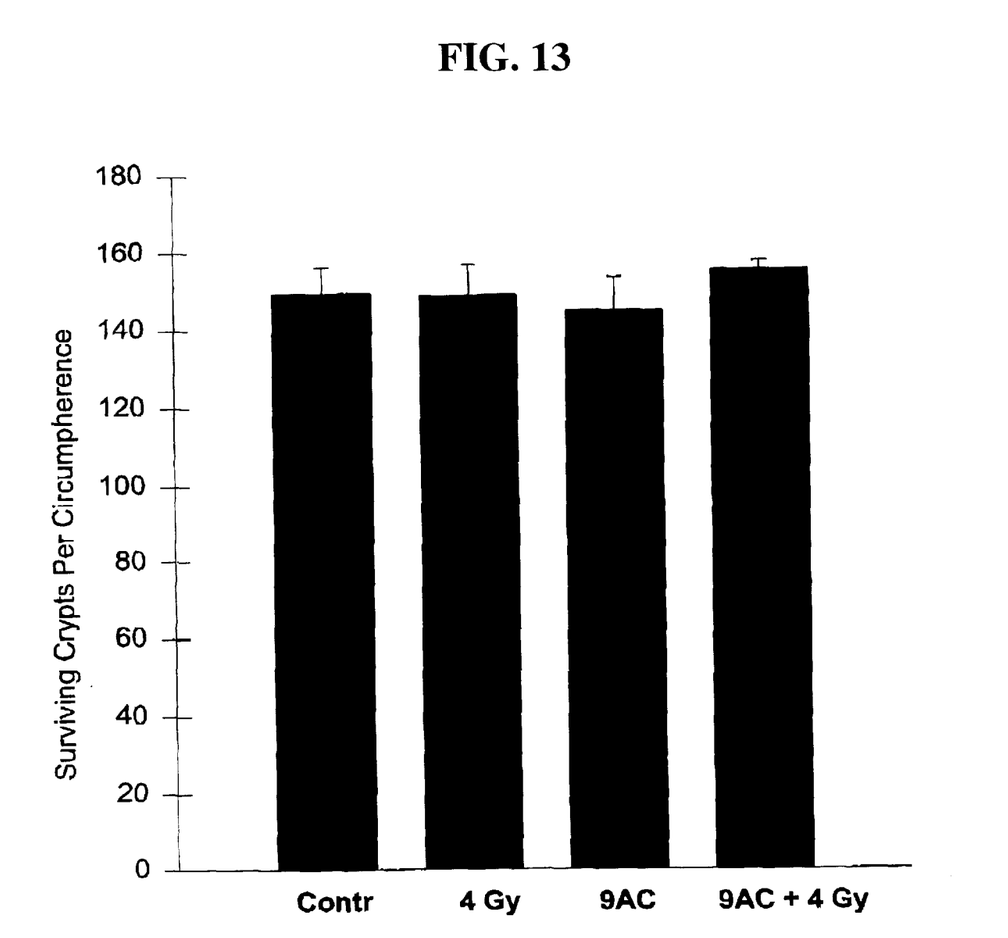
FIG. 13 is a graph depicting the number of surviving crypts/transverse histological section of mouse jejunum after treatments summarized in FIG. 12.

A significant effect of 4 mg/kg 9-aminocamptothecin (9-AC) on the $^{99m}$Tc-pertechnetate jejunal absorption was not observed until 3.5 days postexposure, by which time the absorption rate dropped to 35% of the control level (FIG. 9). Histological examination of the jejunal mucosa indicates that rapid decline in the absorption function on 3.5 days after 9-AC administration coincided with the time of maximal cell loss on the intestinal villi. By this time the mean rate of the $^{99m}$Tc-pertechnetate intestinal absorption was significantly delayed even by single sublethal (½ of the $LD_{10}$) 2 mg/kg 9-AC intramuscular injection (FIG. 10). As seen on FIG. 10 combination of the 4 Gy single sublethal TBI with 2 mg/kg 9-AC injection decreased the jejunal absorption rate in an additive fashion. The influence of irradiation, 9-AC treatment and combined 9-AC plus irradiation on the number of functionally active jejunal cells per villus showed similar pattern as the $^{99m}$Tc-pertechnetate absorption suggesting that the decrease in the intestinal absorption function has a cellular basis (FIG. 11). The additive decrease in the intestinal absorption function on the day 3.5 following combined radiation and 9-AC treatment correlates well with the number of apoptotic cells in the jejunal mucosa (FIG. 12). The classical jejunal microcolony assay failed to show any difference in jejunal crypt survival between the control group and mice treated with irradiation alone, 9-AC alone or its combination (FIG. 13). These data suggest that the major contribution to the cell loss and subsequent malabsorption caused by combined radiation and 9-AC treatment is due to apoptosis.

The invention provides a sensitive functional assay to study radiation, chemotherapy and chemoradiation related damage to the intestinal mucosa. There is a well-defined dose-response relationship and correlation with morphological changes. This method can be used repeatedly for each patient on a daily basis in order to follow-up individually the course of the prescribed chemo-, radiation or chemoradiation treatment regimens and to predict individual sensitivity to the treatment-related acute or late damage to the normal mucosa.

All publications and patents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for assessing the functional integrity of a mucosal membrane, comprising:

(a) locally administering a dosage of a radionuclide to the surface of a mucosal membrane of a mammal; and (b) employing dynamic scintigraphy to measure the rate of absorption of the radionuclide from said surface into the bloodstream of the mammal, wherein a decrease in said rate of absorption provides a measure of the loss of functional integrity of said mucosal membrane.

2. The method of claim 1 wherein the mucosal membrane is in the gastrointestinal tract of the mammal.

3. The method of claim 1 wherein the mucosal membrane is in the mouth, nose, throat or esophagus of said mammal.

4. The method of claim 1 wherein the mucosal membrane is in the urogenital tract of said mammal.

5. The method of claim 1 wherein the mammal is a human.

6. The method of claim 5 wherein the human is a cancer patient.

7. The method of claim 1 wherein, after step (b), the mammal is subjected to radiation therapy comprising irradiation of said mucosal membrane, and steps (a) and (b) are repeated to provide an indication of the loss of said functional integrity.

8. The method of claim 1 wherein, after step (b), the mammal is exposed to chemotherapy, and steps (a) and (b) are repeated, to provide an indication of the loss of said functional integrity.

9. The method of claim 1 wherein, prior to step (a), the mammal is subjected to radiation therapy or chemotherapy, and step (b) provides an indication of the extent of loss of functional integrity of said mucosal membrane.

10. The method of claim 1 wherein the radionuclide is $^{99m}$Tc, $^{75}$Se or a radionuclide of iodine.

11. The method of claim 10 wherein the radionuclide is $^{99m}$Tc.

12. The method of claim 11 wherein the radionuclide is provided by $^{99m}$TcO$^-_4$.

13. The method of claim 1 wherein the rate of absorption into the bloodstream is measured at a site remote from the site of administration.

14. The method of claim 1 wherein the rate of absorption into the bloodstream is measured at the site of administration.

15. The method of claim 13 wherein the remote site is the heart.

16. The method of claim 7 or 8 wherein the rate of absorption of radionuclide decreases following therapy and the decrease is correlated to the extent of damage to said mucosal membrane.

17. The method of claim 16 wherein the decrease in rate of absorption of radionuclide provides a measure of the tolerance of said mammal to therapy.

* * * * *

UNITED STATES PATENT AND TRADEMARK OFFICE
CERTIFICATE OF CORRECTION

PATENT NO.: 6,099,821
DATED: August 8, 2000
INVENTOR(S): Tyvin A. Rich and Alexander V. Kirichenko It is certified that error appears in the above-identified patent and that said Letters Patent is hereby corrected as shown below:

After the title, please insert - - Cross Reference To Related Application This application claims priority from U.S. Provisional Patent Application Serial No. 60/070,550, Filed January 6, 1998- -.

In the Assignee [73], delete "University of Virginia" and "both".

Signed and Sealed this

Twenty-second Day of May, 2001

*Attest:*

NICHOLAS P. GODICI

*Attesting Officer*   *Acting Director of the United States Patent and Trademark Office*